(12) United States Patent
Kobayashi et al.

(10) Patent No.: US 6,337,368 B1
(45) Date of Patent: Jan. 8, 2002

(54) LIPOPROTEIN ADSORBENT AND LIPOPROTEIN ADSORBER MADE WITH THE USE OF THE SAME

(75) Inventors: Akira Kobayashi, Settsu; Tsutomu Okuyama, Kobe, both of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/424,634

(22) PCT Filed: Jun. 3, 1998

(86) PCT No.: PCT/JP98/02442

§ 371 Date: Feb. 28, 2000

§ 102(e) Date: Feb. 28, 2000

(87) PCT Pub. No.: WO98/55224

PCT Pub. Date: Dec. 10, 1998

(30) Foreign Application Priority Data

Jun. 3, 1997 (JP) .............................................. 9-162004
Jul. 1, 1997 (JP) .............................................. 9-191774
Mar. 24, 1998 (JP) ........................................... 10-096611

(51) Int. Cl.$^7$ .......................... A61M 1/36; B01J 20/22; G01N 30/00; G01N 33/92
(52) U.S. Cl. ....................... 525/50; 210/692; 424/78.17; 530/359; 604/5.03
(58) Field of Search ....................... 210/692; 424/78.17, 424/78.27, 78.29; 525/50; 514/7.21; 530/359; 604/5.03

(56) References Cited

U.S. PATENT DOCUMENTS 5,216,127 A * 6/1993 Hirai et al. .................. 530/380

FOREIGN PATENT DOCUMENTS

| JP | 62-82973 A) | * | 4/1987 |
| JP | 62-186940 A) | * | 8/1987 |
| JP | 63-208764 A) | * | 8/1988 |
| JP | 3-152455 A) | * | 6/1991 |
| JP | 6-11322 (B2 | * | 2/1994 |

* cited by examiner

Primary Examiner—Jeffrey E. Russel
(74) Attorney, Agent, or Firm—Connolly Bove Lodge & Hutz LLP.

(57) ABSTRACT

The present invention has its objects to provide an adsorbent capable of efficiently adsorbing and removing LDL and VLDL from various lipoprotein-containing solutions, as well as a lipoprotein adsorber in which the adsorbent is used. This invention is related to a lipoprotein adsorbent which comprises a water-insoluble carrier having, on at least one part of the surface of the carrier, at least one group (other than p-nitrobenzoic acid) selected from the group consisting of groups represented by the general formula, and groups represented by the general formula.

18 Claims, No Drawings

LIPOPROTEIN ADSORBENT AND LIPOPROTEIN ADSORBER MADE WITH THE USE OF THE SAME

TECHNICAL FIELD

The present invention relates to a lipoprotein adsorbent. More particularly, it relates to a lipoprotein adsorbent for selectively adsorbing and removing lipoproteins, including apoB proteins, in particular low density lipoproteins (hereinafter, LDL) and very low density lipoproteins (hereinafter, VLDL), from blood constituents or the like.

BACKGROUND ART

Lipoproteins occurring in blood, in particular LDL and VLDL, commonly known as a villain cholesterol, contain a large amount of cholesterol and are known to be causative of atherosclerosis. On the other hand, the high density lipoprotein (hereinafter, HDL), commonly known as a goody cholesterol, is known to serve as an atherosclerosis retarding factor. Therefore, means is desired by which LDL and VLDL can be removed from blood constituents or the like without removing HDL therefrom.

As the methods currently in clinical use for removing LDL and VLDL, there can be mentioned plasma exchange therapy, double filtration membrane method, use of adsorbents (immobilized dextran sulfate, immobilized anti-apoB antibody, etc.) and HELP system, among others.

However, the membrane method brings about simultaneous removal of a considerable amount of HDL together with LDL and VLDL and therefore fails to satisfy the selectivity for lipoprotein. Further, there is a drawback that plasma proteins are partly removed simultaneously, hence such losses need to be repaired by supplementation.

As the removing method using an adsorbent, there can be mentioned, for example, the removing method using the so-called immunoadsorbent comprising an antibody or the like immobilized and the removing method using an adsorbent comprising a compound having affinity for LDL and VLDL (hereinafter, ligand) as immobilized according to the principle of the so-called affinity chromatography.

The removing method using an immunoadsorbent, however, has problems although it satisfies the selectivity for lipoprotein; thus, for example, the antibody to be used is not readily available or is poor in economy or storage stability or is difficult to sterilize.

In the removing method which uses an adsorbent based on the principle of affinity chromatography, heparin, dextran sulfate and the like are used as ligands of adsorbents. The adsorbents in which these ligands are used show good selectivity for lipoprotein and the ligands themselves are not very expensive. In cases where a ligand is used in large amounts, however, it is desired that said ligand is less expensive.

As an adsorbent for adsorbing and removing lipoproteins by using such an organic compound as phenyl glycidyl ether as a ligand and utilizing the hydrophobic interaction between the phenyl group and the hydrophobic sites of the lipoprotein surface, there is commercially available Phenyl Sepharose CL-4B (product of Pharmacia Fine Chemicals). However, this adsorbent, though it is inexpensive, adsorbs large amounts of HDL as well as LDL and VLDL and thus has a serious drawback from the standpoint of the selectivity for lipoprotein.

DISCLOSURE OF THE INVENTION

In view of the above-mentioned state of the art, the present invention has its objects to provide an adsorbent capable of efficiently adsorbing and removing LDL and VLDL from various lipoprotein-containing solutions, such as blood, serum, plasma, dilutions thereof, and solutions resulting from pretreatment of them for removal of blood corpuscles or serum protein or the like as well as a lipoprotein adsorber in which said adsorbent is used.

Japanese Kokai Publication Sho-62-186940 describes a lipoprotein adsorbent which comprises a water-insoluble carrier having aniline or an aniline derivative immobilized thereon and, in Japanese Kokai Publication Sho-63-208764, there is described a lipoprotein adsorbent comprising a water-insoluble matrix and, on the surface thereof, a group represented by the general formula —NR$^a$R$^b$ in which R$^b$ is a group such that the corresponding compound R$^b$H has a logarithmic value (log P) of 0 to 3.2, P being the partition coefficient in the water-octanol system, and it is disclosed that an inexpensive lipoprotein removing apparatus capable of removing LDL and VLDL selectively can be provided by using said adsorbent.

Referring to these technologies, the present inventors made further investigations and, as a result, found that when the lipoprotein adsorbents having a group represented by the above general formula —NR$^a$R$^b$ further have a substituent in the meta position of R$^b$, which is the aromatic ring-containing atomic group in said group —NR$^a$R$^b$, the selectivity for LDL and VLDL, in particular, is high, that when, in cases where R$^b$ is a group bound to an aromatic ring via an atom or atomic group, it is bound to the aromatic ring via a carbonyl group, the selectivity for LDL and VLDL is high; and that when R$^b$ has a specific functional group, the selectivity for LDL and VLDL is particularly high.

Thus, the present invention provides a lipoprotein adsorbent comprising a water-insoluble carrier having, on at least one part of the surface of said carrier, at least one group (other than p-nitrobenzoic acid) selected from the group consisting of groups represented by the general formula

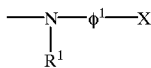

(hereinafter also represented as "—NR$^1$ϕ$^1$X") (wherein R$^1$ represents a hydrogen atom or a methyl or ethyl group, ϕ$^1$ represents an atomic group comprising an aromatic ring bound directly or via one atom to the nitrogen atom, X represents a substituent atom or atomic group bound to a meta position of said aromatic ring, and ϕ$^1$X represents an atomic group such that the compound represented by Hϕ$^1$X has a logP value (P being the partition coefficient in the water-octanol system) of 0 to 3.2), and groups represented by the general formula

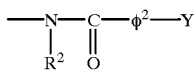

(hereinafter also represented as "—NR$^2$COϕ$^2$Y") wherein R$^2$ represents a hydrogen atom or a methyl or ethyl group, CO represents a carbonyl group, ϕ$^2$ represents an atomic group comprising an aromatic ring bound to the nitrogen atom via said carbonyl group, Y represents an atomic group bound to said aromatic ring, to the exclusion of the case where Hϕ$^2$Y is benzene, and COϕ$^2$Y represents an atomic group such that the compound represented by Yϕ$^2$COH has a logP value of 0 to 3.2 (P being the partition coefficient in the water-octanol system). The present invention further provides a lipoprotein adsorber which comprises an adsorption section containing the lipoprotein adsorbent mentioned above, a liquid inlet section for a liquid to flow into said adsorption section and a liquid discharge section for the liquid that has flown into said adsorption section to flow out of said adsorption section.

DETAILED DESCRIPTION OF THE INVENTION

In the following, the present invention is described in detail.

The lipoprotein adsorbent of the present invention has, on at least one part of the surface of a water-insoluble carrier, at least one group selected from the group consisting of a group represented by the general formula —$NR^1\phi^1X$ (wherein $R^1$, $\phi^1$ and X are as defined above) and a group represented by the general formula —$NR^2CO\phi^2Y$ (wherein $R^2$, CO, $\phi^2$ and Y are as defined above).

In the above group —$NR^1\phi^1X$, $R^1$ represents a hydrogen atom, methyl group or ethyl group. The above-mentioned $\phi^1$ represents an atomic group comprising an aromatic ring bound to the nitrogen atom either directly or via an atom. The above-mentioned X represents an atomic group bound to the meta position of said aromatic ring. Further, $\phi^1X$ resulting from binding $\phi^1$ and X to each other is such that the compound represented by $H\phi^1X$ has a logP value of 0 to 3.2 (P being the partition coefficient in the water-octanol system).

The logP value, which is the logarithmic value of the partition coefficient in the water-octanol system, is a parameter indicative of the degree of hydrophobicity of a compound. A typical method of determining the partition coefficient P is as follows.

The compound is dissolved in octanol (or water), an equal volume of water (or octanol) is added to the solution, and the mixture is shaken on a Griffin flask shaker (product of Griffin and George Limited) for 30 minutes and centrifuged at 2,000 rpm for 1 to 2 hours. The concentrations of the compound in the octanol layer and aqueous layer are determined by any of various methods, for example by spectrophotometry or GLC (gas-liquid chromatography), and the P value is calculated as follows:

$$P = C_{oct}/C_w \qquad (1)$$

where Coct is the concentration of the compound in the octanol layer and Cw is the concentration of the compound in the aqueous layer.

In accordance with the present invention, the logP value for the compound represented by $H\phi^1X$ is 0 to 3.2. If the logP value is less than 0, the hydrophobic interaction with lipoproteins will be weak, hence the adsorbing ability for lipoprotein will be poor. If said logP value exceeds 3.2, not only LDL and VLDL but also HDL and other proteins are simultaneously adsorbed, hence a problem from the selectivity viewpoint will arise. The above range is thus critical. It is preferred that said logP value be 0.8 to 2.7. While it is stated in Japanese Kokai Publication Sho-63-208764 that the hydrophobicity of $\phi^1X$ in the group —$NR^1\phi^1X$ mentioned above plays an important role in the adsorption of lipoproteins, it has now newly been found in the present invention that, in addition to the degree of hydrophobicity, the position of the functional group bound to the aromatic ring is related to the adsorptivity for lipoproteins and that when the adsorbent has the functional group in the meta position, it shows particularly high selectivity as compared with those having the functional group in the ortho or para position.

Said logP value may vary to some extent but not to a great extent depending on the position (ortho, meta, para) of the substituent functional group on the aromatic ring, so that said logP value may be the same as in the case of Japanese Kokai Publication Sho-63-208765.

The term "selective" in this specification means that the adsorptivity of HDL for the adosorbent is low and the adsorptivity for LDL and VLDL is high. The value calculated according to the following formula (2) is used as an index of selectivity.

$$\text{Index of selectivity} = (\% \text{ adsorption of HDL})/(\% \text{ adsorption of LDL}) \qquad (2)$$

The nearer to zero the value of the above formula (2) is, the higher the selectivity is.

The aromatic ring contained in the above-mentioned group $\phi^1$ is not particularly restricted but includes, among others, benzene, pyridine, pyrimidine and triazine rings and condensed rings derived from these.

The above-mentioned compound represented by $H\phi^1X$ is not particularly restricted but may be any compound having a logP value of 0 to 3.2. Thus, for example, when the aromatic ring contained therein is a benzene ring, there may be mentioned toluene, m-xylene, ethylbenzene, phenol, benzyl alcohol, 2-phenylethanol, benzaldehyde, anisole, phenetole, phenylacetic acid, phenoxyacetic acid, methyl benzoate, nitrobenzene, chlorobenzene, bromobenzene, fluorobenzene, m-dinitrobenzene, 3-nitrobenzaldehyde, 3-nitroanisole, 3-nitrotoluene, benzamide, acetophenone, 3-ethylphenol, 3-ethoxyphenol, acetanilide, 3-methylbenzyl alcohol and the like.

When the aromatic ring contained in said $\phi^1$ is a pyridine ring, as said $H\phi^1X$, there can be mentioned, for example, 2-amino-4-fluoropyridine, 2-amino-6-fluoropyridine, 3-amino-5-fluoropyridine, 4-amino-6-fluoropyridine, 2-amino-4-nitropyridine, 2-amino-6-nitropyridine, 3-amino-5-4-nitropyridine, 4-amino-6-nitropyridine, 2-amino-4-hydroxypyridine, 2-amino-6-hydroxypyridine, 3-amino-5-hydroxypyridine, 4-amino-6-hydroxypyridine, 2-amino-4,6-difluoropyridine, 2-amino-4,6-dinitropyridine, 2-amino-4,6-dihydroxypyridine, 4-amino-2,6-difluoropyridine, 4-amino-2,6-dinitropyridine, 4-amino-2,6-dihydroxypyridine, 4-fluoropyridine-2-carboxamide, 6-fluoropyridine-2-carboxamide, 4-nitropyridine-2-carboxamide, 6-nitropyridine-2-carboxamide, 4-hydroxypyridine-2-carboxamide, 6-hydroxypyridine-2-carboxamide, 2-carboxy-4-fluoropyridine, 2-carboxy-6-fluoropyridine, 2-carboxy-4-nitropyridine, 2-carboxy-6-nitropyridine, 2-carboxy-4-hydroxypyridine, 2-carboxy-6-hydroxypyridine and the like.

In cases where the aromatic ring contained in the above $\phi^1$ is a pyrimidine ring, there may be mentioned, as examples of said compound $H\phi^1X$, 2-amino-4-fluoropyrimidine, 2-amino-6-fluoropyrimidine, 4-amino-2-fluoropyrimidine, 4-amino-6-nitropyrimidine, 2-amino-6-nitropyrimidine, 2-amino-4-hydroxypyrimidine, 2-amino-6-hydroxypyrimidine, 4-amino-6-hydroxypyrimidine, 2-amino-4,6-difluoropyrimidine, 2-amino-4,6-dinitropyrimidine, 2-amino-4,6-dihydroxypyrimidine, 4-amino-2,6-difluoropyrimidine, 4-amino-2,6-dinitropyrimidine, 4-amino-2,6-dihydroxypyrimidine 2-carboxy-4-fluoropyrimidine, 2-carboxy-6-fluoropyrimidine, 4-carboxy-2-fluoropyrimidine, 4-carboxy-6-nitropyrimidine, 2-carboxy-6-nitropyrimidine, 2-carboxy-4-hydroxyprimidine, 2-carboxy-6 hydroxypyrimidine, 4-carboxy-6-hydroxypyrimidine and the like.

In cases where the aromatic ring contained in the above $\phi^1$ is a triazine ring, there may be mentioned, as examples of said compound H$\phi^1$X, 2-amino-4,6-difluoro-1,3,5-triazine, 2-amino-4,6-dichloro-1,3,5-triazine, 2-amino-4,6-dinitro-1,3,5-triazine, 2-amino-4,6-dihydroxy-1,3,5-triazine, 2-carboxy-4,6-difluoro-1,3,5-triazine, 2-carboxy-4,6-dichloro-1,3,5-triazine, 2-carboxy-4,6-dinitro-1,3,5-triazine, 2-carboxy-4,6-dihydroxy-1,3,5-triazine, 3-amino-5-fluoro-1,2,4-triazine, 3-amino-5-bromo-1,2,4-triazine, 3-amino-5-chloro-1,2,4-triazine, 3-amino-5-nitro-1,2,4-triazine, 3-amino-5-hydroxy-1,2,4-triazine, 3-carboxy-5-fluoro-1,2,4-triazine, 3-carboxy-5-bromo-1,2,4-triazine, 3-carboxy-5-chloro-1,2,4-triazine, 3-carboxy-5-nitro-1,2,4-triazine, 3-carboxy-5-hydroxy-1,2,4-triazine and the like.

Referring to the above-mentioned group —NR$^1\phi^1$H, from the ligand structure viewpoint, those ligands in which the functional group bound to the aromatic ring is bound to the meta position thereof show higher selectivity for LDL than those ligands in which the functional group is bound to the ortho or para position.

The "meta position" in this specification means the meta position for the aromatic ring of the corresponding —NR$^1\phi^1$H in regard to said —NR$^1\phi^1$X group occurring in the adsorbent of the present invention (thus, in the case of a benzene ring, position 3 or position 5).

The above-mentioned X may be bound to either one of the meta positions of said aromatic ring or both meta positions simultaneously. Further, in the case of the above-mentioned X bound to both meta positions simultaneously, the kind of the above-mentioned X may be the same or different.

Said X is not particularly restricted but includes, for example, nitro, hydroxy, fluoro, bromo, chloro, iodo, methyl, ethyl, methoxy, ethoxy, thiol, cyano, amino, acetyl, hydrazyl, carboxy, isocyanato, isothiocyanato, aldehyde group and the like. In cases where said X can have another substituent, said X may have a further substituent. Among the substituents specifically mentioned above, halogens, and hydroxy, nitro, acetyl, thiol and aldehyde groups are preferred.

The —NR$^1\phi^1$X group has been described above. More specifically, as HNR$^1\phi^1$X corresponding to the compound having the above-mentioned group —NR$^1\phi^1$X, there can be mentioned 3-5-difluoroaniline, m-hydroxybenzylamine, m-nitrobenzylamine, m-fluorobenzylamine, m-hydroxybenzhydrazide, m-nitrobenzhydrazide, m-fluorobenzhydrazide, m-hydroxythiobenzamide, m-nitrothiobenzamide, m-fluorothiobenzamide, m-hydroxybenzenesulfonamide, m-nitrobenzenesulfonamide, m-fluorobenzenesulfonamide, m-hydroxyaniline, m-nitroaniline, m-fluoroaniline, m-mercaptoaniline, m-methoxyaniline, m-aminophenol, m-aminoacetophenone, m-aminoindazole, m-aminobenzyl alcohol, m-hydroxybenzoic acid, m-nitrobenzoic acid, m-fluorobenzoic acid and the like. Among them, 3,5-difluoroaniline, m-aminophenol, m-aminoacetophenone, m-nitroaniline and m-hydroxybenzoic acid are preferred. These may be used singly or two or more of them may be used in combination.

When the lipoprotein adsorbent of the present invention has the above-mentioned group —NR$^1\phi^1$X, selectivity for that is improved, namely the lipoprotein adsorbent has at least about 1.5 times and at most about 7 times higher selectivity when compared, in terms of the selectivity index defined by the above formula (2), with the lipoprotein adsorbents disclosed in Japanese Kokai Publication Sho-63-208764.

The aromatic group of the $\phi^1$ mentioned above is bound to the nitrogen atom of the group —NR$^1\phi^1$X directly or via an atom. In cases where it is bound via an atom, such an atom or atomic group may be a carbon, nitrogen, oxygen, sulfur or phosphorus atom or the like. The nitrogen atom in the above group —NR$^1\phi^1$X is associated with the selectivity difference between LDL and HDL. According to the method of introducing the —NR$^1\phi^1$X group into the water-insoluble carrier, the nitrogen atom in said group —NR$^1\phi^1$X may be one originating from the water-insoluble carrier or one originating from the ligand. For example, (1) when said —NR$^1\phi^1$X group is a group derived from a compound represented by the general formula

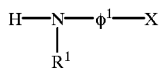

(in which R$^1$, $\phi^1$ and X are as defined above) (hereinafter also expressed as "HNR$^{1\Phi 1}$X") and is immobilized on the water-insoluble carrier via the nitrogen atom of the above-mentioned compound, the nitrogen atom in said —NR$^1\phi^1$X group is of ligand origin and (2) when said —NR$^1\phi^1$X group is a group introduced into a water-insoluble carrier by reacting the water-insoluble carrier having a group represented by the general formula

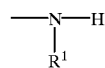

(in which R$^1$ is as defined above) (hereinafter also expressed as "—NR$^1$H") with a compound represented by the general formula Z$\phi^1$X (in which X and $\phi^1$ and X are as defined above and Z represents a functional group capable of reacting with an amino group or a part of said functional group) the nitrogen atom in said —NR$^1\phi^1$X group is of the water-insoluble carrier origin.

Preferred as the compound represented by the above formula HNR$^1\phi^1$X are compounds in which X is a group selected from the group consisting of halogens and hydroxy, nitro, acetyl, thiol and aldehyde groups, and mixtures thereof. The compound represented by the above formula HNR$^1\phi^1$X may be an aniline derivative or a mixture of aniline derivatives, a benzylamine derivative or a mixture of benzylamine derivatives, or the like. These are readily available, hence are particularly useful. The above-mentioned aniline derivative is not particularly restricted but includes, for example, aromatic alkyl-substituted anilines such as m-toluidine and 3,5-xylidine; aromatic alkoxy-substituted anilines such as m-aminoanisole and 3-aminophenetole; anilines having one or more substituents of one or more kinds on the aromatic ring thereof, such as m-chloroaniline, m-bromoaniline, m-fluoroaniline, m-nitroaniline, 3,5-dinitroaniline, 3,5-dichloroaniline, 3,5-dibromoaniline, 3,5-difluoroaniline, m-aminobenzoic acid, ethyl m-aminobenzoate, 3-aminoacetophenone, m-aminophenol, m-aminothiophenol, m-aminophenethyl alcohol, m-aminobenzyl alcohol and m-phenylenediamine; and the like. Among them, 3,5-difluoroaniline, m-aminophenol, 3-aminoacetophenone and m-nitroaniline are preferred. These may be used singly or two or more of them may be used in combination.

Said benzylamine derivative is not particularly restricted but includes, for example, meta-fluorobenzylamine, 3,5- difluorobenzylamine, meta-bromobenzylamine, 3,5-dibromobenzylamine, meta-iodobenzylamine, 3,5-diiodobenzylamine, meta-chlorobenzylamine, 3,5-dichlorobenzylamine, meta-nitrobenzylamine, 3,5-dinitrobenzylamine, meta-hydroxybenzylamine, 3,5-dihydroxybenzylamine, meta-mercaptobenzylamine, 3,5-dimercaptobenzylamine and the like.

The compound represented by the above formula $Z\phi^1 X$ is not particularly restricted but includes, for example, m-hydroxybenzamide, m-nitrobenzaldehyde, m-methoxybenzaldehyde, m-fluorobenzaldehyde, 3,5-dihydroxybenzaldehyde, 3,5-difluorobenzaldehyde, m-mercaptobenzaldehyde, m-nitrobenzoic acid, m-hydroxybenzoic acid, 3,5-dinitrobenzoic acid, m-bromobenzoic acid, m-chlorobenzoic acid, m-fluorobenzoic acid, m-mercaptobenzoic acid, 3,5-dihydroxybenzoic acid, m-aminobenzoic acid and the like. Among them, m-hydroxybenzoic acid is preferred. These may be used singly or two or more of them may be used in combination.

In the above formula $-NR^2CO\phi^2 Y$, $R^2$ represents a hydrogen atom or a methyl or ethyl group. CO represents a carbonyl group. $\phi^2$ represents an atomic group comprising an aromatic ring bound to the nitrogen atom via said carbonyl group. $CO\phi^2 Y$ represents an atomic group such that the corresponding compound represented by $Y\phi^2 COH$ has a logarithmic value logP of 0 to 3.2, P being the partition coefficient in the water-octanol system, (to the exclusion of p-nitrobenzoic acid).

If the logP value of the compound represented by the above $HOC\phi^2 Y$ is less than 0, the hydrophobic interaction with lipoproteins will be weak, hence the lipoprotein adsorbing ability will be low. If said logP value exceeds 3.2, not only LDL and VLDL but also HDL and other proteins will be adsorbed simultaneously, raising a problem from the selectivity viewpoint. The above range is thus critical. It is preferred that said logP value be 0.8 to 2.7.

While it is stated in Japanese Kokai Publication Sho-63-208764 that the hydrophobicity of the aromatic ring-containing atomic group $R^b$ in the group represented by the above general formula $-NR^a R^b$ plays an important role in the adsorption of lipoproteins, it has now newly been found that, from the ligand structure viewpoint, when said group $R^b$ is bound via a CO bond, namely it is the above-mentioned $-NR^2 CO\phi^2 Y$, the selectivity for LDL is higher as compared with the cases where it is bound via a CS bond or $CH_2$ bond and that when the ligand has a specific functional group Y, said selectivity is still higher.

Although the above-mentioned logP value is influenced by the particular functional group (e.g. methylene group, carbonyl group or the like) directly bound to the aromatic ring, said value will not vary much according to the presence or absence of such functional group or the kind thereof.

As the functional group Y, there may be mentioned, for example, halogens and hydroxy, acetyl, thiol, aldehyde, amino and like groups. The aromatic ring contained in the above group $\phi^2$ is not particularly restricted but may be any of the groups mentioned hereinabove in connection with the above $\phi^1$.

As the above group $-NR^2 CO\phi^2 Y$, there may be mentioned, in terms of the corresponding compound $HNR^2 CO\phi^2 Y$, such compounds as m-bromobenzamide, o-bromobenzamide, p-bromobenzamide, m-chlorobenzamide, o-chlorobenzamide, p-chlorobenzamide, m-fluorobenzamide, p-fluorobenzamide, o-iodobenzamide, p-iodobenzamide, m-nitrobenzamide, o-nitrobenzamide, p-nitrobenzamide, m-mercaptobenzamide, o-mercaptobenzamide, p-mercaptobenzamide, m-hydroxybenzamide, o-hydroxybenzamide, p-hydroxybenzamide, 2,4-dihydroxybenzamide, 2,5-dihydroxybenzamide, 2,6-dihydroxybenzamide, 3,5-dihydroxybenzamide, 3,4,5-trihydroxybenzamide, m-aminobenzamide, o-aminobenzamide, p-aminobenzamide and the like. Among these, those having hydoxy, nitro or fluoro as the functional group Y, namely m-hydroxybenzamide, 3,5-dihydroxybenzamide, m-nitrobenzamide, 3,5-dinitrobenzamide, m-fluorobenzamide, 3,5-difluorobenzamide and the like are preferred, and m-hydroxybenzamide, 3,5-dihydroxybenzamide, m-fluorobenzamide and 3,5-difluorobenzamide are more preferred. These may be used singly or two or more of them may be used in combination.

When the lipoprotein adsorbent of the present invention has the above-mentioned group $-NR^2 CO\phi^2 Y$, said adsorbent shows improved selectivity, namely the selectivity index thereof as represented by the formula (2) mentioned above is at least about 2.5 times higher as compared with the lipoprotein adsorbents described in Japanese Kokai Publication Sho-63-208764.

The nitrogen atom in the above group $-NR^2 CO\phi^2 Y$ may be either of water-insoluble carrier origin or of ligand origin according to the method of introducing the above group $-NR^2 CO\phi^2 Y$ into the water-insoluble carrier. For example, (1) when said $-NR^2 CO\phi^2 Y$ group is a group derived from a compound represented by the general formula

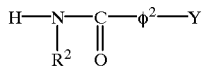

(in which $R^2$, CO, $\phi^2$ and Y are as defined above) (hereinafter expressed also as "$-HNR^2 CO\phi^2 Y$") and immobilized on the water-insoluble carrier via the nitrogen atom in the compound mentioned above, the nitrogen atom in the above $-NR^2 CO\phi^2 Y$ group is of ligand origin.

(2) When said $-NR^2 CO\phi^2 Y$ group is introduced into a water-insoluble carrier by reacting the water-insoluble carrier having a group represented by the general formula

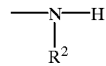

(in which $R^2$ is as defined above) (hereinafter also expressed as "$-NR^2 H$") with a compound represented by the general formula $Y\phi^2 COOH$ (in which Y and $\phi^2$ are as defined above), the nitrogen atom in said $-NR^2 CO\phi^2 Y$ group is of water-insoluble carrier origin.

As the compound represented by the formula $HNR^2 CO\phi^2 Y$, there may be mentioned those specifically given hereinabove.

The compound represented by $\gamma\phi^2 COOH$ is not particularly restricted but includes, for example, those compounds in which one or more groups each selected from the group consisting of halogens, hydroxy, acetyl, thiol, aldehyde and amino are bound to the aromatic ring of $\phi^2$. As specific examples, there may be mentioned m-bromobenzoic acid, o-bromobenzoic acid, p-bromobenzoic acid, m-chlorobenzoic acid, o-chlorobenzoic acid, p-chlorobenzoic acid, m-fluorobenzoic acid, p-fluorobenzoic acid, o-iodobenzoic acid, p-iodobenzoic acid, m-mercaptobenzoic acid, p-mercaptobenzoic acid, o-mercaptobenzoic acid, m-hydroxybenzoic acid, p-hydoxybenzoic acid, o-hydoxybenzoic acid, 2,4-dihydoxybenzoic acid, 2,5-dihydroxybenzoic acid, 2,6-dihydroxybenzoic acid, 3,5-dihydroxybenzoic acid, 3,4,5-trihydroxybenzoic acid, acetylbenzoic acid, acetylaminobenzoic acid, formylbenzoic acid and the like. Among them, m-hydroxybenzoic acid and p-hydroxybenzoic acid are preferred. These may be used singly or two or more of them may be used in combination.

It suffices for at least one of the above-mentioned —$NR^1\phi^1X$ group and —$NR^2CO\phi^2Y$ group to occur on at least one part of the surface of the water-insoluble carrier according to the present invention, and two or more —$NR^1\phi^1X$ and/or —$NR^2CO\phi^2Y$ groups may occur thereon.

The water-insoluble carrier to be used in the practice of the present invention may be an inorganic carrier; an organic carrier such as a carrier comprising a synthetic polymer or a polysaccharide; or a composite carrier comprising an organic carrier and an inorganic carrier. Considering the environment for lipoproteins occurring in the body fluid, a hydrophilic carrier is preferred and, further, the adsorption of substances other than the target substances, namely the so-called nonspecific adsorption should be as little as possible. As such carrier, there may be mentioned, for example, polysaccharides such as crosslinked agarose, crosslinked dextran, crosslinked cellulose, crystalline cellulose, crosslinked chitin and crosslinked chitosan; synthetic polymers such as styrene-divinylbenzene, crosslinked polyvinyl alcohol, crosslinked polyacrylates and crosslinked polyamides; inorganic carriers such as glass beads and silica gel; organic-inorganic composite carriers comprising inorganic carriers, e.g. glass beads, whose surface are coated with a polysaccharide or some other organic macromolecular compound; organic—organic composite carriers comprising organic carriers, comprising synthetic polymers, whose surface are coated with a polysaccharide; and the like.

Said water-insoluble carrier may have a functional group which can be used for an immobilization reaction. As such group, there may be mentioned amino, carboxyl, hydroxy, thiol, aldehyde, halogen, acidanhydride, amide, ester, epoxy, silanol and like groups. As the water-insoluble carrier having the above-mentioned —$NR^1H$ group among such functional groups, for instance, there may be mentioned, for example, water-insoluble carriers comprising materials originally having said —$NR^1H$ group, such as chitosan and the like; and water-insoluble carriers provided with said —$NR^1H$ group by introducing said group into originally amino-free water-insoluble carriers by activating the latter with cyanogen bromide, epichlorohydrin, 1,4-butanediol diglycidyl ether or the like, followed by reaction with a compound represented by the general formula $H_2NR^1$ (in which $R^1$ is as defined above).

Preferably, said water-insoluble carrier is rigid.

The term "rigid" in this specification means that when the water-insoluble carrier is packed uniformly into a cylindrical column and blood, serum or plasma or a dilution thereof or such liquid after pretreatment such as blood corpuscle removal or serum protein removal is passed through the column, said carrier has rigidness to such an extent that consolidation due to carrier deformation or the like will never occur.

If, when a column is packed with the adsorbent of the present invention and incorporated into an extracorporeal circulation circuit, consolidation of the adsorbent occurs during on-line therapeutic treatment, a sufficient rate of flow of body fluid will not be obtained any longer, whereby the treatment period has to be prolonged or it may even become impossible to continue the treatment. To avoid the consolidation of the adosorbent, it is preferred that the adsorbent have a sufficient mechanical strength, namely it be rigid.

The microstructure of the adsorbent of the present invention may be porous or nonporous. For obtaining a high LDL and VLDL adsorbing capacity per unit volume, however, it is preferred that the specific surface area be large, namely the adsorbent be porous, in particular wholly porous.

Said "porous" preferably means that the pore volume amounts to not less than 20% of the apparent volume of the water-insoluble carrier and the specific surface area amounts to not less than $3m^2/g$. Those carriers which fail to meet these requirements are not suited for practical use because of their limited adsorption capacity.

When said water-insoluble carrier is porous, it preferably has an exclusion limit molecular weight of 1 million to 100 million as measured using spherical proteins. When said water-insoluble carrier is porous, its exclusion limit molecular weight of not less than 1 million is used since it is necessary for LDL and VLDL molecules having a molecular weight of not less than 1 million to readily penetrate into pores of the water-insoluble carrier. If the exclusion limit molecular weight is less than 1 million, the adsorption capacity will be small, hence such carrier will be unsuited for practical use. If said exclusion limit molecular weight exceeds 100 million, the adsorbent will become weak in mechanical strength or the solid content of the adsorbent will be too low to have a sufficient adsorption capacity, hence will be unsuited for practical use. Thus, a preferred range is 1 million to 100 million and a more preferred range is 3 million to 70 million.

Said exclusion limit molecular weight is the molecular weight of the smallest molecule among molecules which are incapable of penetrating into pores in gel permeation chromatography, namely are excluded, as described, for example, in the monograph "Jikken Kosoku Ekitai Kuromatografi (Experiments in High Performance Liquid Chromatogarphy)" (Hiroyuki Hatano and Toshihiko Hanai, published by Kagaku Dojin).

The porous carrier mentioned above is not particularly restricted but includes, for example, porous cellulosic carriers, porous chitosan carriers, vinylic porous carriers comprising styrene-divinylbenzene copolymers, crosslinked polyacrylates and crosslinked polyvinyl alcohol; and inorganic porous carriers such as glass, silica, alumina and the like.

As the method of producing the lipoprotein adsorbent of the present invention, there may be mentioned, for example, the method for introducing the above group —$NR^1\phi^1X$ by the method which comprises binding a compound represented by the above formula $HNR^1\phi^1X$ to a water-insoluble carrier via the nitrogen atom in said compound or reacting a water-insoluble carrier having the above-mentioned group —$NR^1H$ with a compound represented by the above $Z\phi^1X$, for instance, or method for introducing the above group —$NR^2CO\phi^2Y$ by the method which comprises binding said compound represented by the formula $HNR2CO\phi^2Y$ to a water-insoluble carrier via the nitrogen atom in said compound or reacting water-insoluble carrier having the above-mentioned group represented by —$NR^2H$ with a compound represented by the above formula $Y\phi^2COOH$ for instance. Further, there can be used the method which comprises introducing the above-mentioned group —$NR^1\phi^1X$ or —$NR^2CO\phi^2Y$ into a water-soluble macromolecular compound and then subjecting the reaction product to crosslinking or like treatment to thereby obtain an adsorbent in the form of a water-insoluble form.

Said water-soluble macromolecular compound is not particularly restricted but includes, among others, polysaccharides such as dextran and starch; polymers such as polyvinyl alcohol and saponification products derived from ethylene-vinyl acetate copolymers with a low ethylene content; and the like.

The adsorbent obtained by the above production method has the above-mentioned —NR$^1\phi^1$X or —NR$^2$CO$\phi^2$Y group introduced into the above-mentioned water-insoluble carrier or the above-mentioned water-soluble macromolecular compound. The method of immobilization is not particularly restricted but may be any of various known ones, such as physical, ionic or covalent bonding.

In the practice of the present invention, however, it is preferred that the ligand is immobilized on said water-insoluble carrier or water-soluble macromolecular compound in the manner of covalent bonding which affords little possibility of ligand leakage. Moreover, if necessary, a spacer may be introduced between the water-insoluble carrier and the ligand, namely the group —NR$^1\phi^1$X or —NR$^2$CO$\phi^2$Y.

The form or shape of the adsorbent of the present invention is not particularly restricted but may be selected from such arbitrary shapes as granules, aggregates of particles, fibers, membranes and hollow fibers.

The adsorbent of the present invention can be used for removing LDL and VLDL from lipoprotein-containing liquids such as blood, serum or plasma, dilutions thereof, or liquids obtained therefrom after such pretreatment as blood corpuscle removal or serum protein removal. More specifically, it can be used as an adsorbent for the treatment of patients with hyperlipidemia or as an adsorbent for the analysis of various lipoproteins.

The adsorber of the present invention comprises an adsorption section containing the lipoprotein adsorbent of the present invention, a liquid inlet section for a liquid to flow into said adsorption section and a liquid discharge section for the liquid that has flown into said adsorption section to flow out of said adsorption section. It is preferred that said adsorber is provided with a filter which said liquid and components contained therein can pass through but the adsorbent of the present invention cannot pass through.

For using the adsorbent of the present invention for therapeutic purposes, various techniques are available. The simplest and easiest technique comprises pooling blood of a patient extracorporeally in a blood bag or the like, admixing the blood with the adsorbent of the present invention to remove LDL and VLDL, removing the adsorbent by passing through a filter and returning the blood to the patient. While this technique does not require any complicated apparatus, the amount of blood per one treatment is small. Moreover, it is time-consuming and troublesome.

Another technique comprises using an adsorber packed with the adsorbent of the present invention.

Specifically, an adsorber comprising a column packed with the adsorbent of the present invention is incorporated in an extracorporeal circulation circuit, and the adsorption and removal are effected on line mode. As said treatment, there can be mentioned the method which comprises circulating plasma whole blood directly through said circuit or the method which comprises separating plasma from blood and passing the plasma through said adsorber. The adsorbent of the present invention and the adsorber in which said adsorbent is used can be used for both modes of treatment.

BEST MODES FOR CARRYING OUT THE INVENTION

The following examples illustrate the present invention in further detail. These examples, however, are by no means limitative of the scope of the present invention.

REFERENCE EXAMPLE 1

Ten milliliters (10 ml; sediment volume) of a porous cellulosic carrier (product of Chisso Corp., exclusion limit molecular weight for spherical proteins; 5.0×10$^7$, mean grain size; 184±24 μm) was taken and washed with about 1 liter of reverse osmosis water. After washing, the carrier was transferred onto a glass filter and dried by 15 minutes of suction using a suction pump. After thorough stirring, 0.131 g (corresponding to 0.2 ml as adsorbent sediment volume) of the carrier was weighed and placed in a microtube (Nunc Co., Cryo Tube, capacity 1.8 ml), 1.5 ml of human serum (product of Kokusai Bio Co.) was added, and the mixture was shaken at 37° C. for 2 hours. After shaking, the supernatant was assayed for total cholesterol (hereinafter, "TC"; using Cholesterol-HR (product of Wako Pure Chemical Industries)), triglycerides (hereinafter, "TG"; using Clinimate TG-2 reagent (product of Daiichi Pure Chemicals Co.)) and HDL-cholesterol (hereinafter, "HDL-C"; using HDL-C Auto "Daiichi" (product of Daiichi Pure Chemicals Co.)). The concentration of LDL-cholesterol (hereinafter, "LDL-C") was calculated from FriedewaldIs formula (Friedewald, W. T., et al., Clin. Chem. 18: 499, 1972) cited below. The concentration of HDL-C was 36 mg/dl and the LDL-C thereof was 146 mg/dl.

$$(LDL-C)=TC-(HDL-C)-1/5TG \qquad \text{Formula (3)}$$

EXAMPLE 1

Forty milliliters (40 ml; sediment volume) of the same porous cellulosic carrier as used in Reference Example 1 (product of Chisso Corp., exclusion limit molecular weight for spherical proteins; 5.0×10$^7$, mean grain size; 184±24 μm) was taken, 40 ml of reverse osmosis water (RO water, Yamato pure line RO 21; product of Yamato Kagaku Co.) was added, and the temperature was raised to 40° C. Thereto was added 12 ml of 20% NaOH, and the mixture was shaken at 40° C. for 30 minutes. Then, 12 ml of epichlorohydrin was added, and the mixture was shaken at 40° C. for further 2 hours to allow the reaction to proceed. After reaction, the carrier was washed with about 2.5 liters of reverse osmosis water, to give an epoxidized carrier. The amount of the thus-introduced epoxy group was 11.3 μmol/g.

To 30 ml of the thus-obtained epoxidized carrier was added a solution (24 ml) of 1 g of 3,5-difluoroaniline in aqueous ethanol and, while allowing the mixture to stand at 50° C., the reaction was allowed to proceed for 6 hours. After reaction, the adsorbent was washed in sequence with ethanol (about 1 liter) and reverse osmosis water (about 2 liters), to give an adsorbent carrying 3,5-difluoroaniline immobilized thereon. The thus-obtained adsorbent was treated in the same manner as in Reference Example 1, and the concentrations of HDL-C and LDL-C were determined in the same manner as in Reference Example 1. Then, the percent adsorptions of different lipoproteins were calculated using the formulas (4) and (5) given below. The results are shown in Table 1. The result of calculation according to the formula (2) given hereinabove as an index of selectivity is also shown in Table 1.

Percent adsorption of HDL=[[(HDL-C concentration in Reference Ex.)−(HDL-C concentration in Ex. or Comparative Ex.)]/ (HDL-C concentration in Reference Example)]×100  (4)

Percent adsorption of LDL=[[(LDL-C concentration in Reference Ex.)−(LDL-C concentration in Ex. or Comparative Ex.)]/ (LDL-C concentration in Reference Ex.)]×100  (5)

EXAMPLE 2

An immobilized m-aminophenol-carrying adsorbent was obtained in the same manner as in Example 1 except that 1.1 g of m-aminophenol was used in lieu of 1.0 g of 3,5-difluoroaniline. The adsorbent obtained was treated in the same manner as in Reference Example 1, and the concentrations of HDL-C and LDL-C were determined. The percent adsorptions of HDL and LDL were calculated in the same manner as in Example 1, and the results are shown in Table 1. The result of calculation according to the above formula (2) as an index of selectivity is also shown in Table 1.

EXAMPLE 3

An immobilized m-aminoacetophenone-carrying adsorbent was obtained in the same manner as in Example 1 except that 1.3 g of m-aminoacetophenone was used in lieu of 1.0 g of 3,5-difluoroaniline. The adsorbent obtained was treated in the same manner as in Reference Example 1, and the concentrations of HDL-C and LDL-C were determined. The percent adsorptions of HDL and LDL were calculated in the same manner as in Example 1, and the results are shown in Table 1. The result of calculation according to the above formula (2) as an index of selectivity is also shown in Table 1.

EXAMPLE 4

An immobilized m-nitroaniline-carrying adsorbent was obtained in the same manner as in Example 1 except that 1.3 g of m-nitroaniline was used in lieu of 1.0 g of 3,5-difluoroaniline. The adsorbent obtained was treated in the same manner as in Reference Example 1, and the concentrations of HDL-C and LDL-C were determined. The percent adsorptions of HDL and LDL were calculated in the same manner as in Example 1, and the results are shown in Table 1. The result of calculation according to the above formula (2) as an index of selectivity is also shown in Table 1.

EXAMPLE 5

To 30 ml of the epoxidized carrier obtained in the same manner as in Example 1 were added 30 ml of reverse osmosis water and 1.5 ml of 30 weight % aqueous ammonia and, after thorough mixing, the mixture was allowed to stand at 40° C. for 2 days to allow the reaction to proceed. After reaction, the carrier was collected by filtration and washed with water to give an aminated carrier (hereinafter, "N-carrier"). The thus-obtained N carrier (30 ml) was subjected to displacement washing on a glass filter with 150 ml of dioxane, 150 ml of 10% by volume triethylamine in dioxane and 300 ml of dioxane in that order and then transferred to a reaction vessel, and a solution of 890 mg of m-hydroxybenzoic acid in 75 ml of dioxane was added. Thereto was added a solution of 300 mg of dicyclohexylcarbodiimide in 6 ml of dioxane, and the reaction was carried out for 3 hours with stirring. Then, a solution of 300 mg of dicyclohexylcarbodiimide in 6 ml of dioxane was further added, and the reaction was carried out for 3 hours with stirring. Thereafter, the adsorbent was recovered by filtration and washed with dioxane, methanol, dioxane and water in the order mentioned to give an N-adsorbent carrying m-hydroxybenzoic acid as immobilized thereon. The adsorbent obtained was treated in the same manner as in Reference Example 1, and the concentrations of HDL-C and LDL-C were determined. The percent adsorptions of HDL and LDL were calculated in the same manner as in Example 1, and the results are shown in Table 1. The result of calculation according to the above formula (2) as an index of selectivity is also shown in Table 1.

COMPARATIVE EXAMPLE 1

An immobilized p-aminophenol-carrying adsorbent was obtained in the same manner as in Example 1 except that 1.1 g of p-aminophenol was used in lieu of 1.0 g of 3,5-difluoroaniline. The adsorbent obtained was treated in the same manner as in Reference Example 1, and the concentrations of HDL-C and LDL-C were determined in the same manner as in Reference Example 1. The percent adsorptions of HDL and LDL were calculated in the same manner as in Example 1, and the results are shown in Table 1. The result of calculation according to the formula (2) given hereinabove as an index of selectivity is also shown in Table 1.

COMPARATIVE EXAMPLE 2

An immobilized p-aminoacetophenone-carrying adsorbent was obtained in the same manner as in Example 1 except that 1.3 g of p-aminoacetophenone was used in lieu of 1.0 g of 3,5-difluoroaniline. The adsorbent obtained was treated in the same manner as in Reference Example 1, and the concentrations of HDL-C and LDL-C were determined. The percent adsorptions of HDL and LDL were calculated in the same manner as in Example 1. The results are shown in Table 1. The result of calculation according to the above formula (2) as an index of selectivity is also shown in Table 1.

COMPARATIVE EXAMPLE 3

An immobilized p-nitroaniline-carrying adsorbent was obtained in the same manner as in Example 1 except that 1.3 g of p-nitroaniline was used in lieu of 1.0 g of 3,5-difluoroaniline. The adsorbent obtained was treated in the same manner as in Reference Example 1, and the concentrations of HDL-C and LDL-C were determined in the same manner as in Reference Example 1. The percent adsorptions of HDL and LDL were calculated in the same manner as in Example 1, and the results are shown in Table 1. The result of calculation according to the above formula (2) as an index of selectivity is also shown in Table 1.

EXAMPLE 6

An immobilized p-hydroxybenzoic acid-carrying adsorbent was obtained in the same manner as in Example 5 except that 890 mg of p-hydroxybenzoic acid was used in lieu of 890 mg of m-hydroxybenzoic acid. The adsorbent obtained was treated in the same manner as in Reference Example 1, and the concentrations of HDL-C and LDL-C were determined. The percent adsorptions of HDL and LDL were calculated in the same manner as in Example 1, and the results are shown in Table 1. The result of calculation according to the above formula (2) as an index of selectivity is also shown in Table 1.

EXAMPLE 7

An immobilized m-nitrobenzoic acid-carrying adsorbent was obtained in the same manner as in Example 5 except that 1.0 g of m-nitrobenzoic acid was used in lieu of 890 mg of m-hydroxybenzoic acid. The adsorbent obtained was treated in the same manner as in Reference Example 1, and the concentrations of HDL-C and LDL-C were determined. The percent adsorptions of HDL and LDL were calculated in the same manner as in Example 1. The results are shown in Table 1. The result of calculation according to the above formula (2) as an index of selectivity is also shown in Table 1.

COMPARATIVE EXAMPLE 4

An immobilized benzylamine-carrying adsorbent was obtained in the same manner as in Example 1 except that 1.0 g of benzylamine was used in lieu of 1.0 g of 3,5-difluoroaniline. The adsorbent obtained was treated in the same manner as in Reference Example 1, and the concentrations of HDL-C and LDL-C were determined in the same manner as in Reference Example 1. The percent adsorptions of HDL and LDL were calculated in the same manner as in Example 1, and the results are shown in Table 1. The result of calculation according to the above formula (2) as an index of selectivity is also shown in Table 1.

COMPARATIVE EXAMPLE 5

An immobilized thiobenzamide-carrying adsorbent was obtained in the same manner as in Example 1 except that 1.3 g of thiobenzamide was used in lieu of 1.0 g of 3,5-difluoroaniline. The adsorbent obtained was treated in the same manner as in Reference Example 1, and the concentrations of HDL-C and LDL-C were determined in the same manner as in Reference Example 1. The percent adsorptions of HDL and LDL were calculated in the same manner as in Example 1, and the results are shown in Table 1. The result of calculation according to the above formula (2) as an index of selectivity is also shown in Table 1.

TABLE 1

|  | % Adsorption of HDL | % Adsorption of LDL | Index of selectivity* |
|---|---|---|---|
| Example 1 | 11 | 42 | 0.26 |
| Example 2 | 11 | 54 | 0.20 |
| Example 3 | 5 | 33 | 0.15 |
| Example 4 | 9 | 34 | 0.26 |
| Example 5 | 1 | 27 | 0.05 |
| Example 6 | 3 | 25 | 0.12 |
| Example 7 | 3 | 21 | 0.14 |
| Compar. Ex. 1 | 12 | 15 | 0.80 |
| Compar. Ex. 2 | 3 | 3 | 1.0 |
| Compar. Ex. 3 | 0 | 0 | — |
| Compar. Ex. 4 | 23 | 62 | 0.37 |
| Compar. Ex. 5 | 12 | 11 | 1.1 |

*Index of selectivity for lipoproteins (based on the result of calculation according to the formula (2))

From Table 1, it is seen that, as for the adsorption of lipoproteins, the lipoprotein adsorbent of the present invention is low in percent adsorption of HDL and high in percent adsorption of LDL, hence has high selectivity.

INDUSTRIAL APPLICABILITY

The lipoprotein adsorbent of the present invention, which has the constitution mentioned hereinabove, can adsorb and remove LDL and VLDL selectively from blood constituents or the like.

What is claimed is:

1. A lipoprotein absorbent which comprises a water-insoluble carrier having, on at least one part of the surface of said carrier, at least one group other than p-nitrobenzoic acid selected from the group consisting of groups represented by the general formula,

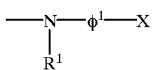

which is a group derived from a compound represented by the formula

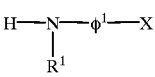

which is selected from the group consisting of 3,5-difluoroaniline, m-hydroxybenzylamine, m-nitrobenzylamine, m-fluorobenzylamine, m-hydroxybenzhydrazide, m-nitrobenzhydrazide, m-fluorobenzhydrazide, m-hydroxythiobenzamide, m-nitrothiobenzamide, m-fluorothiobenzamide, m-hydroxybenzenesulfonamide, m-nitrobenzenesulfonamide, m-fluoroaniline, m-mercaptoaniline, m-methoxyaniline, m-aminoacetophenone, m-aminoindazole, m-aminobenzyl alcohol, and groups represented by the general formula,

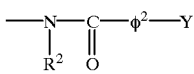

wherein $R^2$ represents a hydrogen atom or a methyl or ethyl group, CO represents a carbonyl group, $\phi^2$ represents a group consisting of atoms comprising an aromatic ring bound to the nitrogen atom via said carbonyl group, Y represents a group consisting of atoms bound to said aromatic ring, to the exclusion of the case where $H\phi^2Y$ is benzene, and $CO\phi^2Y$ represents a group consisting of atoms such that the corresponding compound represented by $Y\phi^2COH$ has a logP value, P being the partition coefficient in a water-octanol system, of 0 to 3.2.

2. The lipoprotein adsorbent according to claim 1, wherein the group represented by the general formula,

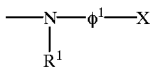

is immobilized on said water-insoluble carrier via the nitrogen atom in said compound.

3. The lipoprotein adsorbent according to claim 1, wherein the group represented by the general formula,

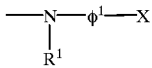

is a group introduced into said water-insoluble carrier by reacting a water-insoluble carrier having a group represented by the general formula,

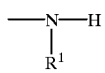

with a compound represented by the general formula $Z\phi^1 X$ wherein Z represents a functional group capable of reacting with an amino group or a part of said functional group.

4. The lipoprotein adsorbent according to claim 1, wherein the compound represented by the general formula,

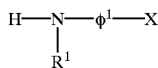

is at least one aniline derivative selected from the group consisting of 3,5-difluoroaniline, m-fluoroaniline, m-mercaptoaniline, m-methoxyaniline, m-aminoacetophenone and m-aminobenzyl alcohol.

5. The lipoprotein adsorbent according to claim 1, wherein the compound represented by the general formula,

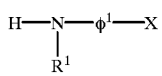

is at least one benzylamine derivative selected from the group consisting of m-hydroxybenzylamine, m-nitrobenzylamine and m-fluorobenzylamine.

6. The lipoprotein adsorbent according to claim 3, wherein the compound represented by the general formula $Z\phi^1 X$ is at least one benzoic acid derivative selected from the group consisting of m-hydroxybenzamide, m-nitrobenzaldehyde, m-methoxybenzaldehyde, m-fluorobenzaldehyde, 3,5-difluorobenzaldehyde, m-mercaptobenzaldehyde, m-nitrobenzoic acid, m-hydroxybenzoic acid, m-fluorobenzoic acid and m-mercaptobenzoic acid.

7. The lipoprotein adsorbent according to claim 1, wherein the group represented by the general formula,

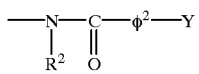

is a group derived from a compound represented by the general formula,

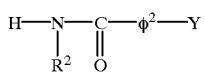

and is immobilized on a water-insoluble carrier via the nitrogen atom in said compound.

8. The lipoprotein adsorbent according to claim 1, wherein the group represented by the general formula,

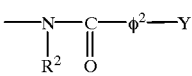

is a group introduced into a water-insoluble carrier by reacting said water-insoluble carrier having a group represented by the general formula,

with a compound represented by the general formula $Y\phi^2 COOH$.

9. The lipoprotein adsorbent according to claim 8, wherein the compound represented by the general formula, $Y\phi^2 COOH$ is a compound or a mixture thereof wherein Y is one or more groups selected from the group consisting of halogen atoms and hydroxy, acetyl, thiol, aldehyde and amino groups.

10. The lipoprotein adsorbent according to claim 1, wherein the water-insoluble carrier is a hydrophilic carrier.

11. The lipoprotein adsorbent according to claim 1, wherein the water-insoluble carrier is rigid and porous.

12. The lipoprotein adsorbent according to claim 11, wherein the water-insoluble carrier has an exclusion limit molecular weight, as determined by using spherical proteins, of 1 million to 100 million.

13. A lipoprotein adsorber which comprises an adsorption section containing the lipoprotein adsorbent according to claim 1, a liquid inlet section for a liquid to flow into said adsportion section and liquid discharge section for the liquid that has flown into said adsportion section to flow out of said adsportion section.

14. The lipoprotein adsorbent according to claim 2 wherein the water-insoluble carrier is a hydrophilic carrier.

15. The lipoprotein adsorbent according to claim 3, wherein the water-insoluble carrier is a hydrophilic carrier.

16. The lipoprotein adsorbent according to claim 4, wherein the water-insoluble carrier is a hydrophilic carrier.

17. The lipoprotein adsorbent according to claim 5, wherein the water-insoluble carrier is a hydrophilic carrier.

18. The lipoprotein adsorbent according to claim 6, wherein the water-insoluble carrier is a hydrophilic carrier.

* * * * *